(12) United States Patent
Bischoff et al.

(10) Patent No.: US 8,486,054 B2
(45) Date of Patent: Jul. 16, 2013

(54) OPTOMETRIST CLIENT

(75) Inventors: Mark Bischoff, Jena (DE); Joachim Fiedler, Crailsheim (DE); Holger Maeusezahl, Jena (DE); Patrick Nast, Gera (DE)

(73) Assignee: Carl Zeiss Meditec AG, Jena (DE)

( * ) Notice: Subject to any disclaimer, the term of this patent is extended or adjusted under 35 U.S.C. 154(b) by 895 days.

(21) Appl. No.: 12/558,852

(22) Filed: Sep. 14, 2009

(65) Prior Publication Data

US 2011/0066143 A1 Mar. 17, 2011

(51) Int. Cl.
*A61B 18/18* (2006.01)
(52) U.S. Cl.
USPC ............................................. 606/4; 351/246
(58) Field of Classification Search
USPC .................... 351/246, 200–204; 606/4–6
See application file for complete search history.

(56) References Cited

U.S. PATENT DOCUMENTS

2007/0161972 A1* 7/2007 Felberg et al. ................. 606/4

OTHER PUBLICATIONS

Carl Zeiss Meditec at the European Congress for Ophthalmology ESCRS (European Society of Cataract and Refractive Surgeons) 2008: Look forward! Carl Zeiss Press Release.
CRS-Master by Carl Zeiss Medictec AG.
Visante OCT with Corneal Topography by Carl Zeiss Medictec AG.
Visante™ OCT, Anterior Segment Imaging & Biometry, A New Perspective in Clinical Confidence by Carl Zeiss Medictec AG.

* cited by examiner

*Primary Examiner* — James Greece
(74) *Attorney, Agent, or Firm* — Leydig, Voit & Meyer, Ltd.

(57) ABSTRACT

A method of providing optometric parameters for an optometric procedure includes locating patient identification information on a central data storage by transmitting a search query from a computing device communicating with the central data storage. The search query generates a result set containing at least one patient having patient identification information substantially matching the search query. From the result set, a patient undergoing the optometric procedure is selected. An input form for this patient is then displayed with input fields corresponding to each of the optometric parameters. A qualified collector obtains the measurement values for the optometric parameters and inputs them into respective input fields. A data record containing the measurement values and the patient identification information is generated and transmitted to the central data storage. The data record can then be transmitted to a planning tool communicating with the central data storage for performing the optometric procedure.

20 Claims, 2 Drawing Sheets

OPTOMETRIST CLIENT

FIELD OF THE INVENTION

The present invention relates generally to optometry, and more specifically to a system and method for obtaining, storing and transferring optometric measurement data.

BACKGROUND OF THE INVENTION

In order correct sight defects, such as myopia, hyperopia and astigmatism, optometrists and/or ophthalmologists perform refractive laser eye surgery on a patient's cornea. Owing to the high level of precision that is required for consistently successful operations, optometrists must accurately determine the type and extent of defects, or aberrations, for each patient prior to laser correction. Consequently, patients undergoing corneal treatment for sight defects are subjected to a wide array of tests to determine various optometric parameters unique to the particular patient. Data consisting of optometric parameters such as radii of curvature, pupil size, cornea size, pupillary distances (near, intermediate and distant), lens segment type, optical transmittance, channel width, sphere power, cylinder power and axis, prism power and base (vertical and horizontal), viewing distances, etc. assist in precisely describing a patient's eye including lower and higher-order aberrations. This data is later used by optometrists and/or ophthalmologists in various procedures or operations. For example, the data can be used to determine an ablation pattern for an excimer laser in a refractive laser eye surgery such as laser-assisted in situ keratomileusis (LASIK).

In determining the various optometric parameters, optometrists typically have many different measuring devices at their disposal, such as lensmeters, autorefractors, phoropters, ophthalmotonometry, corneal topographers, wavefront aberrometers, etc. Each of these devices presents the ascertained measurement data in different ways and utilizes widely varied techniques to document the results, such as displaying, e.g., on a monitor, or printing. Further, these devices, which obtain different optometric parameters, are designed and manufactured by different entities and have little to no compatibility with one another. Moreover, each device utilizes unique customized displays for patient information, measurement values and other data. The different ways of displaying the data can result in confusion and misinterpretation.

In addition to the measurement devices, certain optometric parameters are determined manually and/or require a subjective determination of a trained employee. Patient identification information such as name, maiden name, date of birth, social security number, driver's license number, address, patient identification number and the like are normally provided in a standard handwritten form filled out by the patient or transcribed by hand prior to the patient's examination by a qualified employee. Various other examination methods also carried out by qualified employees, such as optometrists, ophthalmologists or opticians, are performed manually, at least in part, and provide standard forms for recording measurement values by hand. For example, an attending physician typically uses corrective lenses (probe glasses) and other aids in making a subjective refraction determination and records the measurement results by hand on a standard form suited for that purpose.

In order to provide a single source for this data, it is usually transcribed by hand and/or read off the customized displays and is manually entered into a patient's medical records by medical personnel. In addition to being time-consuming, the transfer of data from the various different measurement devices entails a substantial risk of error, misinterpretation, data loss, conversion and patient mix-up. For example, measurement values could be read off or transcribed inaccurately or the handwritten measurement values could be misinterpreted, e.g., due to poor handwriting, or entered wrong into the patient's medical records.

This risk is also compounded by a subsequent manual transfer of requisite measurement data from a patient's medical records to other devices, such as a surgical planning tool for creating an ablation pattern of a refractive laser eye surgery or cut geometry for femtosecond-refractive treatments (FLEx/SMILE). Since the diagnostic data is used in planning a correction of sight defects, it must be ensured that the data is both accurate and recent. However, with the data being entered from multiple sources and being transferred to multiple different devices, it is difficult to maintain accuracy throughout the different stages. This is especially true in the typical case where multiple different medical personnel (from clerks and assistants to ophthalmologists) and patients are involved. From obtaining the requisite diagnostic data to planning a surgery, multiple handwritten records are created by different people which other persons transferring the data must interpret and enter correctly at each phase.

One planning tool, CRS-MASTER by Carl Zeiss Meditec AG, integrates measurement data from an aberrometer and corneal topographer into an electronic planning system for a refractive laser eye surgery. While such a planning tool is designed for automated import of data created by compatible measurement devices and helps to minimize the risk of error, the electronic planning is still normally preceded by an initial handwritten documentation phase. This may be due to the fact that some measurements are performed manually without access to the planning tool. Further, diagnostic data from incompatible measurement devices must still be obtained and transferred along with the other handwritten documentation to a patient's medical records. This could result in a segregation of data and still entails the same initial risk of loss or error.

The recording of measurement values by hand and the manual transfer of data from multiple different measurement devices (having different viewing apparatuses and utilizing different forms of data display) to medical records and/or from the medical records to a surgical planning tool entails a substantial risk of clerical and transcription errors such as misinterpretation, e.g., of writing or of the particular data display, or data loss/conversion during a subsequent manual transfer. Specifically, the following errors can arise during the following steps from diagnosis to treatment:

Step 1, obtaining patient identification data and measurement values: Error 1 (ERR1), an error occurs when assigning recorded data to a patient; Error 2 (ERR2), an error occurs when reading off data from a measurement device; or Error 7 (ERR7), an error occurs when there is no assignment of the measurement data by a qualified collector.

Step 2, transferring the measurement data to a patient's medical records: Error 3 (ERR3), an error occurs when manually entering the data into the respective medical record; or Error 6 (ERR6), an error occurs when temporally assigning the optometric parameters.

Step 3, transferring the measurement data from medical records to a diagnostic or planning tool: Error 4 (ERR4), an error occurs when data in the medical record is misinterpreted; Error 5 (ERR5), an error occurs when manually entering the data into the tool during the computer-assisted processing; Error 6 (ERR6), an error occurs when temporally assigning the optometric parameters; or Error 7 (ERR7), an error occurs when there is no assignment of the measurement data by a qualified collector.

To illustrate the various errors that can occur at different stages from acquiring measurement values to loading them into a planning tool, the following scenario is useful. A collector of data takes an optometric parameter using a measurement device which results in a measurement value of 10.0 dpt for that optometric parameter. However, when transferring the measurement value to the patient's medical record, the location of the data point is inadvertently moved due to an error in reading or transcription such that the measurement value now appears as 1.00 dpt. Then, when consulting the patient's medical record to program the diagnostic data into a planning tool, it is again misinterpreted such that the value of 1.00 dpt is inadvertently read out as 7.00 dpt.

To minimize the risk of such errors, frequent, time-consuming control steps are customarily utilized which typically involve many burdensome manual comparisons and an onerous system of cross-checking data.

SUMMARY OF THE INVENTION

Therefore, a simple and effective method of obtaining, storing and transferring measurement data, which also avoids handwritten records and manual transfers, is needed. By decreasing the risk of error, such a system is able to provide a higher rate of success in optometric procedures.

In an embodiment, the present invention provides a secure method of obtaining optometric parameters for an optometric procedure. Patient identification information stored on a central data storage is searched remotely from a computing device communicating with the central data storage. The search generates a result set containing at least one patient having patient identification information substantially matching the search query. From the result set, the patient undergoing the optometric procedure is selected. An input form for this patient is then displayed on the computing device with input fields corresponding to each of the optometric parameters. A qualified collector obtains the measurement values for the optometric parameters (e.g., from running tests on various measuring devices or performing a subjective refraction) and inputs them into respective input fields. A data record containing the measurement values and the patient identification information is generated on the computing device and transmitted to the central data storage. The data record can then be transmitted to a planning tool communicating with the central data storage for performing the optometric procedure.

BRIEF DESCRIPTION OF THE DRAWINGS

The foregoing and other features of the present invention will be more readily apparent from the following detailed description and drawings of illustrative embodiments of the invention in which.

DETAILED DESCRIPTION OF THE PREFERRED EMBODIMENTS

Figure 1:
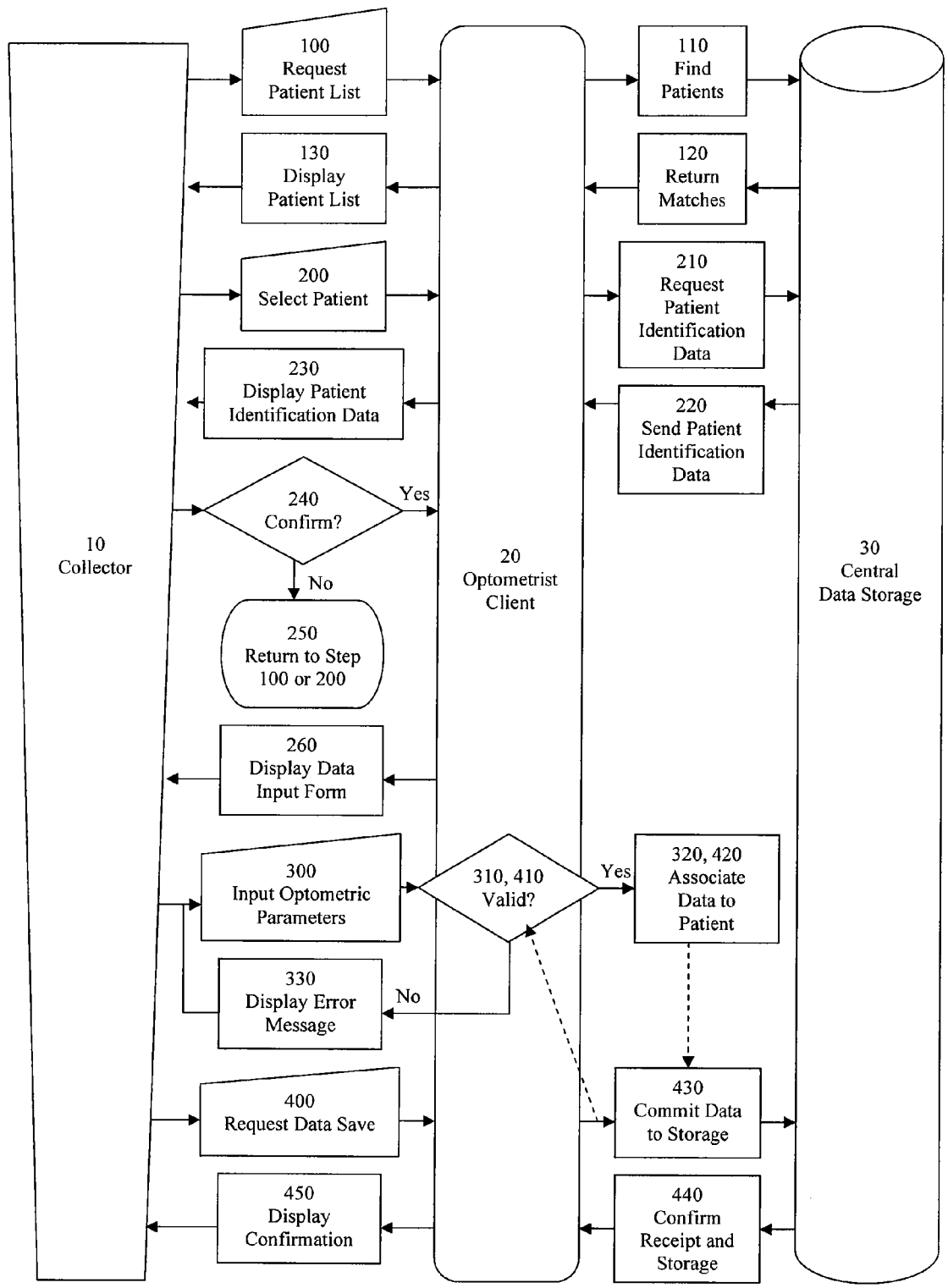
FIG. 1 is a process flowchart illustrating the steps of the method according to an embodiment of the present invention.

Referring to FIG. 1, a collector 10 is assigned to a patient undergoing an optometric procedure, such as a refractive laser eye surgery. The collector 10 may be an optometrist, ophthalmologist, optician, medical assistant or another qualified employee. Each collector 10 may also be assigned a collector identification number and/or a password in order to prevent unauthorized access to the optometrist client 20 by unqualified collectors 10 and/or to identify the collector in resulting data records. If the optometrist client 20 is not able to verify that the collector 10 is qualified, it may disallow input or mark any resulting data records.

The optometrist client 20 is installed as application software on a computing device, such as a personal computer (PC) or a hand-held computing device, having input means, such as a keyboard, mouse, touch-screen and/or other kind of pointing device. A central data storage 30 communicates, e.g., via Universal Serial Bus (USB, USB2); Ethernet (including Gigabit Ethernet); FireWire (IEEE-Standard 1394); wireless local network (WLAN); Bluetooth; Infrared or wide-area cellular telephone networks, with one or more computing devices installed with the optometrist client 20. The central data storage 30 is preferably a mass storage device formed of hard disks, floppy disks, flash memory, optical discs, magneto-optical discs, magnetic tape, drum memory or the like.

After logging in to the optometrist client 20 and verifying that the collector 10 is qualified to collect measurement data, the optometrist client 20 displays one or more search boxes. The collector 10 acquires patient identification information from the patient, personal knowledge or documents which will be used as a query in a search box for locating the patient. A search box may be provided for each category of patient identification information and/or a full system search box could be provided for all categories. Further, the search could allow the collector 10 to enter various filter criteria, such as to display male patients only, to display patients who are scheduled for an appointment on the current day, to display patients who are to be treated with a specific device or who are assigned to a specific diagnostic/treatment procedure or program.

At step 100, the collector 10 enters the patient identification information into the search box corresponding to its respective category or into the full system search box. Possible categories of patient identification information includes name (first and last), maiden name, sex, date of birth, social security number, driver's license number, address, patient identification number, date of registration, date/time of appointment, date of procedure, device that will be used for the procedure, etc.

In one embodiment, the patient identification information may be anthropometric or biometric information, such as a fingerprint or iris scan. In this case, the collector 10 would not have to input a search query at step 100; instead, the optometrist client 20 could be connected to a scanner or other device for acquiring the biometric information directly from the patient. In another embodiment, the patient identification information is information stored in electronic form on an electronic insurance card or patient card and/or associated with an electronic identifier such as a bar code or radio-frequency identifier (RFID) tag. As is the case with the biometric information, this electronic information can be obtained using an appropriate scanning device associated with the optometrist client 20 rather than through manual input.

Once the search query has been entered into the optometrist client 20 or the biometric or electronic information has been obtained, the optometrist client 20 issues the query to central data storage 30 at step 110. In this step, the query is formulated by the optometrist client 20 and transmitted to the central data storage 30 in a standardized or proprietary query syntax, such as Structured Query Language (SQL), Extensible Markup Language (XML), Health Level Seven (HL7) standard or Digital Imaging and Communications in Medicine (DICOM) standard. Preferably, in order to increase efficiency, the search query requests only data which is required for a general representation and/or for uniquely identifying the individual entries. For example, if the search query is the surname of the patient, only particular patient identification information, or specifically just the category corresponding to patient name, is requested. In other words, just the unique data may be returned.

At step 120, the requested data is transmitted to the optometrist client 20. Preferably, this requested data is evaluated by the optometrist client 20 and displayed in the form of a patient list to the collector 10 at step 130. Alternatively, the unique data may be birth dates, appointment dates, etc. and could be displayed in other suitable forms, such as in a tree structure or table. The patient list may consist of one name, multiple names or no names at all depending on the number of matches to the query. For example, if the query is a search for a patient's date of birth of Jan. 1, 1980, a list of all patients stored in the central data storage 30 having that birth date is returned. The collector 10 then selects the appropriate patient off the list at step 200, e.g., by pressing a key, clicking on it with a mouse, selecting it on a touchscreen or employing an alternative pointing device. If just one patient name is returned, the optometrist client 20 could instead automatically select that patient and allow the collector 10 to verify (e.g., by displaying the patient's name and allowing the functionality to return to step 100 if the selected patient is not correct).

If none of the data saved on the central data storage 30 matches the requested data, no matches would be returned in step 120 and a blank list or an error message would be displayed to the collector at step 130. Alternatively, the central data storage could return data which is close to the requested data. In any case, if the patient can not be found on the patient list, the collector 10 is provided the option to return to step 100 or to enter new information in the case of a new patient. If the collector 10 is aware that the patient is new, he or she could choose to enter their patient identification information from the outset, which the optometrist client 20 will commit to storage in the central data storage 30.

Once the collector 10 selects the patient in step 200, the optometrist client 20 issues another query to the central data storage 30 in step 210. The parameters of this query correspond to the unique data that was selected by the collector 10 from the list of matches which, in the embodiment described above, is the patient's name. As in step 110, the query is formulated by the optometrist client 20 and transmitted to the central data storage 30 in a standardized or proprietary query syntax. Also as in step 110, the query preferably requests only data which may be used to uniquely identify the patient.

At step 220, the central data storage 30 runs the query on its database to determine a result set matching the search criteria which is transmitted to the optometrist client 20. This result set preferably contains more information for uniquely identifying a patient (i.e., patient identification information) than in the previous matches returned at step 120. For example, all patient identification information contained in the central data storage 30 for a particular patient could be transmitted to the optometrist client 20 at step 220 while only, e.g., patients' names, are transmitted in step 120. The result set containing the patient identification information is then displayed to the collector 10 at step 220 in a suitable form (e.g., text, lists, tables, photographs, etc.) on a suitable display device (e.g., a monitor or print-out) associated with the optometrist client 20.

If the result set generated in step 220 contains more than one patient, the collector 10 selects the appropriate patient in step 240. However, since ordinarily a particular patient is chosen in step 200, the collector 10 need only review the patient identification information in the result set at step 240 to confirm that it is unique to the patient undergoing examination, e.g., by clicking on an accept button or pressing an appropriate key on a keyboard. If the result set is empty, an error message is displayed at step 230 and/or the collector 10 is presented a form for inputting the patient identification information. If the result set does not correspond to the patient undergoing examination, the collector 10 is prompted to select a different patient in step 200 or to enter other patient identification information in step 100.

In another embodiment of the present invention, all patient identification information associated with a particular patient in the central data storage 30 is transmitted to the optometrist client in step 120 and displayed to the collector 10 in step 130. In this case, steps 200-230 would not be necessary and the collector 10 could merely select the appropriate patient (if more than one patient matches the query in step 120) or confirm that the patient identification information corresponds to the patient undergoing examination (if just one patient matches the query in step 120) at step 240. This is particularly advantageous where the central data storage 30 does not contain data for a large number of patients or where the data is parsed by particularly unique identifying features such as social security number or biometric information. For example, if a collector 10 enters a patient's social security number in step 100, only that particular patient's identification information is transmitted to the optometrist client 20 in step 120 since no two social security numbers are the same. Likewise, the collector 10 could specify at step 100 what information he or she would like returned such as a patient list only or full patient information.

Once the identity of the patient has been confirmed in step 240, the optometrist client 20 presents an input form at step 260 to aid the collector 10 in entering measurement data. The input form preferably consists of labeled input fields which are finable by the collector 10. Each labeled input field corresponds to an optometric parameter such as current lens values, Zernike coefficients, wavefront, radii of curvature, pupil size, cornea size, the position of the pupil relative to specific limbus features, optic axis location, width of accommodation, night and bright-light vision, contrast values, corneal power values, pachymetry, intraocular pressure, pupillary distances (near, intermediate and distant), lens segment type, optical transmittance, channel width, sphere power, cylinder power and axis, prism power and base (vertical and horizontal), viewing distances, dominant eye, monovision-acceptance, medications, findings, etc. Additionally, each field of the input form may be grouped. For example, the input fields may be grouped by necessary, normal and optional data entries. In this case, all necessary input fields must contain an acceptable data entry to proceed. The optometric parameters which are typically determined and documented prior to a refractive laser eye surgery, such as sphere, cylinder, cycloplegic, axis and the objective refraction from an autorefractor, are each associated with an input field. Accordingly, the optometrist client 20 is able to link these parameters to other features for patient and eye identification.

Further, the fields of the input form may be associated with graphical elements and organized as, e.g., index cards, a foldable list, a foldable tree structure, etc. Preferably, the optometrist client 20 presents at least two data forms for each patient; one for the left eye and one for the right eye. This avoids confusion and helps organize diagnostic data by eye since most optometric parameters require measurement values for each eye. However, the measurement values for each eye could also be entered into a single input form as well.

The input forms presented in step 260 may be provided with one or more identifying features unique to the particular patient. For example, a picture of the patient captioned with the patient's name could be provided at the top or corner of the input form. Likewise, the forms corresponding to the right and left eyes could be provided with topographical images of the right and left eye of the patient, respectively.

Additionally, the input forms presented in step 260 are adapted to the lighting conditions of the examination room where the collector 10 is taking measurements. For example, if a collector 10 is performing a subjective refraction, the input form will typically have to be brightness adapted to be more visible and readable while also not disturbing the measurement. This is done because the data being entered at step 300, and later being verified at step 310, should be clear and readable by the collector 10.

At step 300, the collector 10 obtains measurement values for the optometric parameters by performing various tests and/or procedures manually or on various measurement devices and enters the measurement values into corresponding input fields on the input form. For example, the collector 10 can determine a subjective refraction manually using lenses and other aids. Additionally, the collector 10 can determine optometric parameters using measurement devices such as lensmeters, autorefractors, phoropters, ophthalmotonometry, corneal topographers, wavefront aberrometers, OCT-devices, confocal laser scanners, fundus cameras, etc. In one embodiment, measurement devices are associated and communicate with the optometrist client 20 via a wired (e.g., Ethernet, USB, FireWire, etc.) or wireless (WiFi, Bluetooth, Infrared, etc.) connection such that values are transferred directly from the measurement device to the appropriate data entry field corresponding to the optometric parameter being measured. However, when the input fields are manually filled in by the collector 10, this is accomplished using a keyboard, stylus, touchscreen, multi-touch screen or other input device connected to the computing device loaded with the optometrist client 20. In most cases, the measurement value is a number or text, but in one embodiment, the collector 10 may input pictures, photographs, graphs, images or the like as well. For example, the collector 10 could input a topographical image of the cornea or a wavefront image. In this case, the optometrist client 20 could be provided with image and/or text recognition software.

Each time the collector 10 enters a measurement value into a correspondingly labeled input field of the input form, the optometrist client 20 runs a validity check on the value entered at step 310. In one embodiment, the optometrist client 20 is provided with a valid range of values for each optometric parameter (e.g., many parameters can not be zero and are limited by the size and shape of human eyes). If the particular measurement value entered by the collector 10 falls outside this valid range of values, an error message is displayed by the optometrist client 20 at step 330 and returns for the collector 10 to enter the value again at step 300. The error message may also be an auditory signal as well, such as a beep. If, on the other hand, the measurement value falls within the valid range, the optometrist client 20 associates that value with the patient at step 320, e.g., by linking the optometric parameter to patient identification information or generating a data record which assigns the measured values to the patient. In the case of generating a data record, the data record is produced in an appropriate syntax, such as SQL, XML or standards by HL7 or DICOM. In addition, at step 310, the optometrist client 20 also runs a general plausibility check for the measurement value in the field of optometry and compares it to other measurement values.

Once the collector 10 is done inputting measurement values for the optometric parameters, he or she requests that the data be saved to the central data storage 30 at step 400, e.g. by clicking on a button or pressing a key on the keyboard. Then, at step 430, the optometric client transmits the data to central data storage 30 in standardized or proprietary transfer syntax, such as SQL, XML or standards by HL7 or DICOM. In one embodiment, the optometric client transmits the data record generated in step 320 consisting of the patient identification information and the measured values.

However, in other embodiments indicated by the dashed arrows in FIG. 1, the collector 10 enters all measurement values for the optometric parameters before they are validated at step 310 and/or associated to the patient at step 320. In this case, all optometric parameters are validated and/or associated to the patient at steps 410 and 420, respectively. Additionally, a plausibility check may be performed at step 410 which compares measurement values against one another to determine whether they are optometrically possible (e.g., more than one type of aberration at the same location). A data record is generated by the optometrist client 20 at step 420 containing the measurement values and the associated patient identification information in an appropriate syntax which data record is transmitted to the central data storage 30 at step 430.

In another embodiment, the data record generated in step 320 is transmitted to the central data storage 30 at step 430 each time a measurement value is entered. In this case, the data record is updated on the central data storage 30 as measurement values come in for the optometric parameters. This ensures that the diagnostic data will not be lost by continuously saving it both locally and in the central data storage 30. Such an arrangement is particularly advantageous where there are long breaks between inputting optometric parameters, where the optometrist client 20 is communicating wirelessly from a remote device, where two or more optometrist clients 20 are working in parallel, or where the optometrist client 20 is loaded onto a troublesome computing device.

If the data record has been successfully stored in the central data storage 30, a confirmation message is transmitted in the appropriate syntax to the optometrist client 20 at step 440. The optometrist client 20 then displays a confirmation message to the collector 10 at step 450, e.g., as text on a monitor, a print-out or as an auditory signal. Additionally, the optometrist client 20 may display, or control or trigger a print-out of, the full data record containing the optometric parameters and associated patient identification information. If, on the other hand, it is not successfully stored, an error message indicating the cause of the failure may instead be sent to the optometrist client 20 at step 440 and displayed to the collector 10 at step 450.

Figure 2:
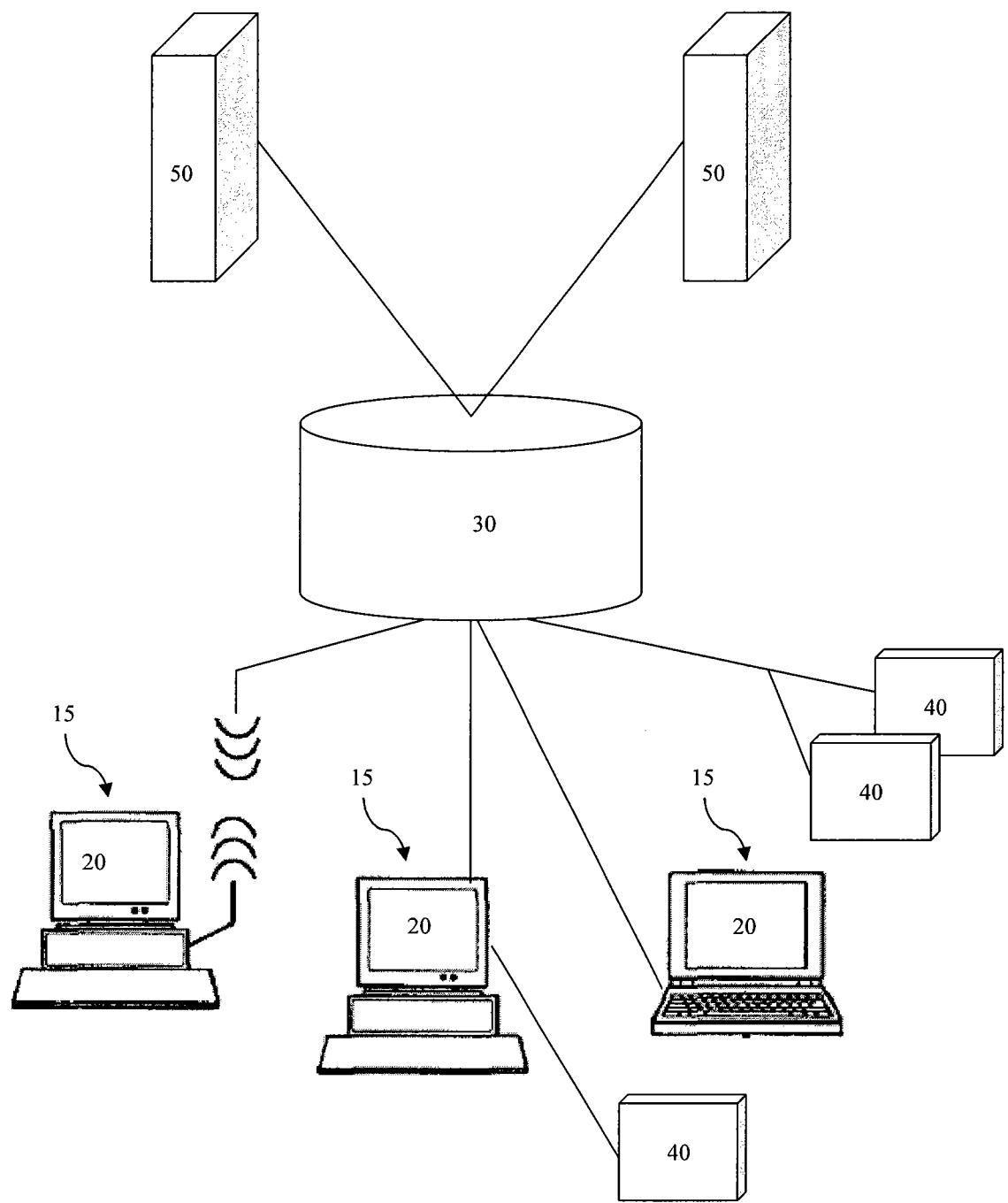
FIG. 2 is a system diagram according to an embodiment of the present invention.

Each time a measurement value is entered and verified at steps 300 and 310, respectively, that measurement value is secured as the corresponding optometric parameter. In other words, once verified, there is no chance that the measurement value will change since it is entered into a data record generated by the optometrist client 20 at step 320 and associated to the patient's identification information. This data record is securely transmitted in appropriate syntax to the central data storage at step 430, thereby preserving the exact measurement values. As seen in FIG. 2, planning tools 50 are connected and communicate with the central data storage 30 so that a patient's data record can be once again securely transmitted in appropriate syntax without risk of error. To further illustrate this point, a collector 10 enters a value of 10.0 dpt as a measurement value for a particular optometric parameter which is verified as valid and plausible by the optometrist client 20 and, after this initial step of entering, the value of 10.0 dpt is never manually written, input, manipulated, interpreted or transcribed throughout the remainder of the process; rather, it is securely electronically transferred as part of a data record.

Referring to FIG. 2, the central data storage 30 is connected to a plurality of computing devices 15, such as a PC or laptop, loaded with the optometrist client 20. The computing devices 15 may also be portable and/or operated by a stylus such as a tablet PC, smart phone or personal digital assistant (PDA). Such devices are intuitive and ergonomic, making data entry by a collector 10 relatively simple on a reduced outlay.

In one embodiment, the central data storage 30 is also connected to a plurality of measurement devices 40 and allows for data transfers therebetween. In yet another embodiment, one or more of the computing devices 15 is connected with one or more measurement devices 40 for directly capturing a measurement value and inputting it into its correspondingly labeled input field. One or more planning tools 50, such as the control for a refractive laser, or other optometric equipment are connected to the central data storage 30 for retrieving data records containing the optometric parameters for a particular patient. On either side, the connection to the central data storage 30 may be a temporary or permanent connection such as a wireless connection using infrared or radio signals, USB or other cable connection. Where a temporary connection is utilized, the measurement values can be recorded offline in data records generated by the optometrist client 20 in a decentralized process on the computing device 15. In this case, a second synchronization step is carried out in which a connection is at least temporarily provided between the computing device 15 and either the central data storage 30 or the planning tool 50. The central data storage 30 and one or more other components may be physically located on the same hardware. For example, the central data storage 30 may be running on the same computing device as the optometrist client 20.

The measurement values may also be provided with a time stamp either in the data record generated by the optometrist client 20 at step 320 or upon storage to the central data storage 30 at step 430. This time stamp indicates the date and/or time that the values were obtained in the central data storage 30 such that the planning tool 50 may disallow a measurement value that is too old (e.g., six months or more) or indicate to its user the problems associated with using old measurement value.

While the invention has been particularly shown and described with reference to preferred embodiments thereof, it will be understood by those skilled in the art that various changes in form and details may be made therein without departing from the spirit and scope of the invention.

What is claimed is:

1. A method of providing optometric parameters for an optometric procedure, the method comprising:
receiving a search query of patient identification information into a computing device communicating with and located remotely from a central data storage, the central data storage containing the patient identification information particular to a plurality of individual patients;
transmitting the search query to the central data storage;
generating a result set containing at least one patient having patient identification information substantially matching the search query;
selecting a patient undergoing the optometric procedure from the result set;
displaying an input form for the patient undergoing the optometric procedure, the input form having input fields corresponding each of the optometric parameters;
receiving measurement values for the optometric parameters into the respective input fields;
associating the patient identification information of the patient undergoing the optometric procedure to the measurement values; and
storing the measurement values in association with the patient identification information in the central data storage.

2. The method according to claim 1, further comprising the step of validating the measurement values after receiving each measurement value.

3. The method according to claim 2, wherein validating the measurement values comprises checking each measurement value against a valid range of values for the respective optometric parameter.

4. The method according to claim 3, wherein validating the measurement values further comprises running a general plausibility check and comparing each measurement value with other measurement values to locate conflicting measurement values.

5. The method according to claim 1, further comprising the step of transmitting the measurement values and associated patient identification information from the central data storage to a planning tool for the optometric procedure.

6. The method according to claim 5, wherein the optometric procedure is a refractive laser eye surgery and the planning tool uses the measurement values to generate a customized ablation pattern.

7. The method according to claim 1, further comprising the step of obtaining the measurement values for the optometric parameters of the patient undergoing the optometric procedure prior to inputting, wherein the measurement values are collected from at least one of measurement devices and a subjective refraction by a collector.

8. The method according to claim 7, further comprising the step of authorizing the collector as qualified to determine the measurement values prior to inputting.

9. The method according to claim 1, wherein associating the patient identification information to the measurement values comprises generating a data record having the measurement values and associated patient identification information, the data record being transmitted to the central data storage for storing.

10. The method according to claim 9, wherein the measurement values are obtained by a qualified collector and the collector is indicated in the data record.

11. The method according to claim 9, wherein the data record includes at least one time stamp indicating a time of measurement for the measurement values.

12. The method according to claim 11, further comprising the step of transmitting the data record from the central data storage to a planning tool for the optometric procedure.

13. The method according to claim 1, further comprising the step of transmitting the patient identification information for the patient undergoing the optometric procedure from the central data storage to the computing device prior to inputting the measurement values, and wherein the result set is a patient list containing a portion of the patient identification information which is unique to the search query.

14. A system of obtaining, storing and securely transferring optometric parameters for an optometric procedure, the system comprising:

a plurality of computing devices each having an input device, the computing devices having an optometrist client configured to receive measurement values for the optometric parameters from the respective input devices;

a central data storage communicating with and located remotely from the computing devices, the central data storage containing patient identification information particular to a plurality of individual patients and being configured to receive data records from the computing devices; and at least one planning tool communicating with the central data storage and being configured to receive the data records from the central data storage, and wherein the data records are generated by the optometrist client and contain the measurement values and the patient identification information of a patient undergoing the optometric procedure.

15. The system according to claim 14, wherein the optometrist client provides an input form having input fields corresponding to the optometric parameters, the input fields being fillable by a collector using one of the input devices for receiving the measurement values.

16. The system according to claim 14, wherein the optometric procedure is a refractive laser eye surgery and the at least one planning tool is configured to generate a customized ablation pattern from the data records.

17. The system according to claim 14, further comprising measurement devices communicating with at least one of the computing devices and the central data storage.

18. The system according to claim 14, wherein the data records include a time stamp corresponding to a time that the optometrist client received the measurement values.

19. The system according to claim 14, wherein the computing devices include at least one of a personal computer, a laptop, a tablet personal computer, a personal digital assistant and a smart phone, wherein the input devices include at least one of a keyboard, a mouse, a touchpad and a touchscreen, and wherein the central data storage is a mass storage device.

20. A method of obtaining optometric parameters for an optometric procedure, the method comprising:

locating patient identification information contained in a central data storage having patient identification information particular to a plurality of individual patients for a particular patient undergoing the optometric procedure based on a search query containing the patient identification information of the particular patient received from a computing device communicating with and located remotely from the central data storage;

displaying an input form having input fields corresponding to each of the optometric parameters on a display of the computing device;

receiving measurement values for the optometric parameters of the patient undergoing the optometric procedure into the respective input fields from an input device of the computing device;

validating the measurement values by comparing them to a valid range of values for each optometric parameter;

generating a data record containing the measurement values and the patient identification information for the patient undergoing the optometric procedure;

storing the data record in the central data storage; and transmitting the data record from the central data storage to a planning tool for the optometric procedure.

* * * * *